United States Patent
Korin

Patent Number: 5,935,431
Date of Patent: Aug. 10, 1999

[54] ULTRAVIOLET OZONE WATER PURIFIER FOR WATER DISINFECTION

[76] Inventor: Amos Korin, 16 Mountainview Dr., Weston, Conn. 06883

[21] Appl. No.: 08/784,210

[22] Filed: Jan. 15, 1997

[51] Int. Cl.⁶ ...................................................... C02F 1/78
[52] U.S. Cl. ......................... 210/205; 210/209; 210/435; 210/443; 422/186.3; 433/80
[58] Field of Search .................................. 210/748, 760, 210/198.1, 205, 209, 435, 443; 422/186.3; 433/80

[56] References Cited

U.S. PATENT DOCUMENTS

| | | |
|---|---|---|
| 4,141,830 | 2/1979 | Last ........................................ 210/760 |
| 4,156,652 | 5/1979 | Wiest ..................................... 210/760 |
| 4,179,616 | 12/1979 | Coviello et al. ...................... 210/760 |
| 4,230,571 | 10/1980 | Dadd ..................................... 210/760 |
| 5,101,399 | 3/1992 | Watanabe et al. . | 
| 5,158,454 | 10/1992 | Viebahn et al. . |
| 5,204,004 | 4/1993 | Johnston et al. . |
| 5,208,933 | 5/1993 | Lustig et al. . |
| 5,230,624 | 7/1993 | Wolf et al. . |
| 5,266,215 | 11/1993 | Engelhard . |
| 5,370,534 | 12/1994 | Wolf et al. . |
| 5,401,399 | 3/1995 | Magusson et al. . |
| 5,474,451 | 12/1995 | Dalrymple et al. . |
| 5,474,748 | 12/1995 | Szabo . |
| 5,536,400 | 7/1996 | Schultz . |
| 5,556,279 | 9/1996 | Wolf et al. . |
| 5,573,666 | 11/1996 | Korin . |

OTHER PUBLICATIONS

Article entitled "Disinfection—Liquid Purification by UV Radiation, and its Many Applications", Ultrapure Water, Sep. 1991, pp. 1–8 authored by Jesse Rodriguez and Steve Gagnon.
Article entitled "UV For Residential Applications", Water Technology, Oct. 1988, 4 pp., authored by Bill Sax.
CDC Press Advisory entitled "CDC, EPA Issue Drinking Water Guidance for People With Weakened Immune Systems", Jun. 15, 1995, pp. 1–2.

*Primary Examiner*—Jay H. Woo
*Assistant Examiner*—Betsey J. Morrison
*Attorney, Agent, or Firm*—Ohlandt, Greeley, Ruggiero & Perle

[57] ABSTRACT

An integrated filtration and sterilization apparatus including an ultraviolet lamp disposed within an ultraviolet radiation permeable sleeve such that a gas conduit is formed between an outer surface of the ultraviolet lamp and an inner surface of the sleeve; a filtration member disposed about the sleeve such that a permeate chamber is formed between an outer surface of the sleeve and an inner surface of the filtration member; a feed chamber disposed about an outer surface of the filtration member; a liquid feed for feeding a liquid to the feed chamber and a liquid removal line for removing liquid from the permeate chamber; a gas feed for feeding an oxygen-containing gas to the gas conduit and a gas removal line for removing an ozone-containing gas from the gas conduit; and a mixing device for mixing liquid removed from the permeate chamber and ozone-containing gas from the gas conduit downstream from the permeate chamber.

15 Claims, 3 Drawing Sheets

ULTRAVIOLET OZONE WATER PURIFIER FOR WATER DISINFECTION

The present invention relates generally to a filtration and sterilization apparatus with an integrated ozone-generating means for generating ozone used to post treat a filtered and sterilized liquid. More specifically, the present invention is directed to an integrated apparatus which is capable of filtering particulate, organic materials, inorganic materials and/or heavy metal materials from a water stream, and sterilizing the filtered water stream to destroy most microorganisms, bacteria and viruses contained therein by UV radiation treatment, in which the UV radiation source is also used to generate an ozone supply that is injected into the filtered and sterilized water stream to prevent the formation of biofilms in downstream waterlines.

BACKGROUND OF THE INVENTION

As environmental agencies become more aware of the potential health risks associated with drinking either municipal or well water, there has been an every increasing need for residential water purification systems which are capable of removing organics, inorganics, particulate, microorganisms, bacteria and viruses from the water supply prior to consumption. Most conventional systems require a series of filtration and chlorination units to properly remove such matters from the water. These units are extremely costly to install and maintain, and take up a lot of space making them unfit for countertop use.

Filtration media has been used for years to remove particulate from the water supply, while carbon block filters have been effective in removal of organics and inorganics. However, conventional filters are incapable of removing microorganisms such as bacteria, viruses, yeasts or molds. Ultraviolet radiation in the 200–300 nanometer range have been extremely effective in killing such microorganisms. As such, germicidal lamps have been used extensively in air and water purification, sewage treatment, protection of food and beverages, and other disinfection and sterilization applications.

Water purification systems which combine the disinfection and sterilization capabilities of ultraviolet radiation with the particulate, organic and inorganic filtering capabilities of conventional filter media are known. Such combined systems provide extremely pure and sterilized drinking water regardless of the origin of the water source.

Even when such water purification systems are used, however, it has been found that bacteria remains in the water and microbial biofilms can form in pipes downstream of the system. Biofilms are formed when bacteria adheres to a hard surface in an aqueous environment. Over a period of time, microbes entering the pipe stick to the already existing bacterial layer thereby forming a microbial matrix. This matrix, once established, supplies nutrients required for growing additional microbial mass. The formation of biofilms is most pronounced in pipes formed of organic substances such as plastic and rubber, and in pipes having narrow inside diameters.

Although biofilm formation is encountered in most piping systems, the problem is particularly acute in dental unit water lines, as such water lines are usually formed of small diameter plastic tubing. Further, because the water is used in dental work, the prevention of the colonization of the dental unit water lines with bacteria is of particular importance. Nonetheless, biofilm growth has been observed inside new dental unit plastic water lines in as little as two weeks. These biofilms, when viewed through a scanning electron microscope were found to be characterized by microorganisms embedded in an amorphous matrix. The observed amorphous matrix was about 30 to 50 microns thick and capable of shedding bacteria (normal size of about 1 micron) into the water supply. *Pseudomonas aeruginosa* biofilm quantified by measuring distributions of thickness in biofilm samples demonstrated a mean of 33 microns (range of 13.3 microns to 60.0 microns). Most biomass tend to detach in the form of multicellular particles with some particles exceeding 100 microns in size. Large numbers of Gram-negative bacili are commonly found to be present in the water outflow/effluent of dental units. Although some organisms enter the system as occasional contaminants of the main water supply, the high counts observed are due to colonization and growth on the walls of the small bore plastic tubing of the dental unit water lines.

The most widely used method for killing microorganisms in water, and preventing the formation of biofilms, involves treating the water with chlorine. However, disinfection treatments with chlorine can produce a wide variety of byproducts, many of which have been shown to cause cancer and other toxic effects. Ozone is an extremely strong oxidant and is one of the most powerful water sanitizers readily available. Ozone deactivates bacteria and viruses 3125 times faster than chlorine.

The prior art teaches the treatment of unfiltered water with ultraviolet radiation and subsequent treatment with ozone. This prior art further teaches the use of the ultraviolet radiation source as a means for generating the ozone. Such treatments were disadvantageous, however, as without filtration, the pathogen level in the water remains high, and particulate matter, turbidity and other interfering constituents in the water reduces the efficacy of ultraviolet radiation treatment. The entrainment of ozone with water after filtration with a separate media filter, before treatment with ultraviolet light was also heretofore known. Some of these prior art units have used the ultraviolet light source to simultaneously radiate the water, and supply a source of ozone which was then entrained in the water feedstream. The injection of ozone before exposure to ultraviolet light is disadvantageous, however, as ultraviolet radiation can break down ozone, thereby decreasing the efficacy of the ozone treatment.

Two stage water purification systems as discussed above require periodic maintenance such as replacing the carbon block filter approximately every six months (more frequently if needed), replacing the ultraviolet lamp every twelve months to insure proper performance (i.e., lamp may not burn-out, but disinfection capacity does diminish over time), and cleaning of the quartz tube every six months. Although the carbon block filter is easy to replace, i.e., simply unscrew the filter housing and slide the filter off the stainless steel sleeve at the open end, replacement of the ultraviolet lamp requires substantial disassembly of the base unit of the housing. Since the ultraviolet lamp replacement is extremely difficult, many unsophisticated end-users (i.e., homeowners) will tend to simply replace the separate carbon-block filter and not replace the lamp as frequently as necessary. If the lamp is not replaced on a periodic basis its effectiveness in disinfecting and sterilizing water will diminish over time, thus posing a health risk to unwary end-users.

Therefore, it would be highly desirable to have a single unit that includes each of a media filter, an ultraviolet radiation source and an ozone treatment means, that uses the ultraviolet radiation source to simultaneously generate the ozone needed for ozone treatment. It would also be highly desirable to provide an integrated purification unit that optimally treats the water feedstream by filtering the water through a media filter, exposing the filtered water to ultraviolet radiation to kill the majority of microorganisms, and subsequently treat the filtered and radiated water with ozone to neutralize any remaining bacteria to prevent formation of biofilms and contamination in downstream waterlines. In this regard, the present inventor has developed an integrated unit that treats a water stream in the optimal manner by filtering the water through a media filter, subjecting the filtered water to ultraviolet radiation treatment, and subsequently treating the filtered and radiated water with ozone. The ultraviolet light generating source is further used to generate the needed supply of ozone, thereby reducing the complexity, cost, bulk and energy requirements of the unit. Having the carbon microfilter upstream of the ultraviolet light source offers the following advantages:

Preventing harmful cysts such as Cryptosporidium and Giardia liamblia from entering the treated water.

Increasing the efficiency of the ultraviolet radiation treatment by increasing the optical clarity of the water.

Removing ozone scavenging compounds from the water, thereby increasing the disinfection efficiency of the ozone.

Preventing fouling of the quartz tube by preventing biocolloids and other foulants from entering the water.

The present invention also provides many additional advantages which shall become apparent as described below.

SUMMARY OF THE INVENTION

An integrated filtration and sterilization apparatus comprising an ultraviolet lamp disposed within an ultraviolet radiation permeable sleeve, such that a gas conduit is formed between the ultraviolet lamp and the sleeve, a filtration member disposed about the sleeve such that a permeate chamber is formed between the sleeve and the inner surface of the filtration member, a feed chamber disposed about the filtration member, a gas feed for feeding an oxygen-containing gas to the gas conduit, the wavelength of the ultraviolet light source being adjusted such that ultraviolet radiation emanating therefrom simultaneously sterilizes the filtered liquid and generates ozone from the oxygen-containing gas, means for removing the filtered and sterilized liquid from the permeate chamber, means for removing the ozone-containing gas from the gas conduit and means for contacting the filtered and sterilized liquid with the ozone-containing gas at a location downstream from the permeate chamber.

Another embodiment according to the present invention involves an integrated biofilm control system for dental unit waterlines comprising the above-described filtration and sterilization apparatus. Other and further objects, advantages and features of the present invention will be understood by reference to the following specification in conjunction with the annexed drawings.

DESCRIPTION OF THE PREFERRED EMBODIMENTS

Figure 1:
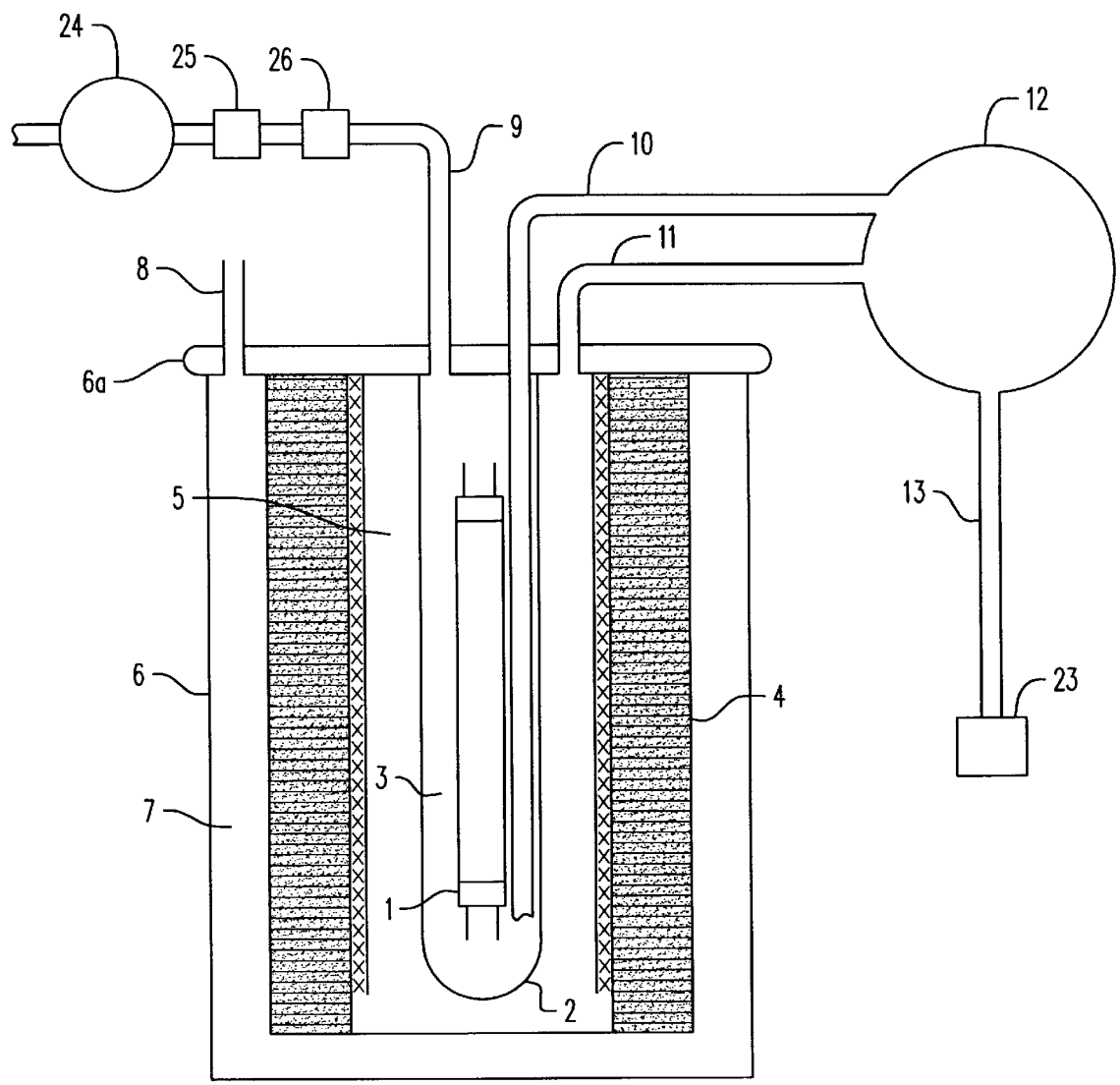
FIG. 1 is a schematic cross-sectional view of the integrated filtration and sterilization apparatus attached inline with a dental unit waterline according to the present invention.

The present invention can best be described by referring to the drawings attached hereto. FIG. 1 depicts an integrated filtration and sterilization apparatus as used as part of a dental unit water supply system. The integrated filtration and sterilization apparatus comprises: an ultraviolet lamp 1, disposed within an ultraviolet radiation permeable sleeve 2, such that a gas conduit 3 is formed between ultraviolet lamp 1 and an inner surface of ultraviolet radiation permeable sleeve 2. A filtration member 4 is disposed around ultraviolet radiation permeable sleeve 2 such that a permeate chamber 5 is formed between an outer surface of ultraviolet radiation permeable sleeve 2 and an inner surface of filtration member 4. An outer housing 6 surrounds filtration member 4 such that a feed chamber 7 is formed between an inner surface of outer housing 6 and an outer surface of filtration member 4. One or both ends of outer housing 6 can be sealed against an end plate 6a, formed with suitable connections for liquid feed 8, gas feed 9, gas removal line 10, liquid removal line 11, and a power cord (not shown) for supplying power to ultraviolet lamp 1.

Untreated liquid is fed to feed chamber 7 through a liquid feed 8. An oxygen-containing gas is simultaneously fed to gas conduit 3 through a gas feed 9. Gas feed 9 can include a pump or blower 24. The oxygen-containing gas can be conditioned by passing the gas through an air drying device 25 and/or an oxygen concentrating device 26. An electrical source (not shown) is required to provide power to ultraviolet lamp 1. In operation, the untreated liquid passes from feed chamber 7 through filtration member 4 to provide a filtered liquid to permeate chamber 5. In permeate chamber 5, the filtered liquid is subjected to ultraviolet radiation generated by ultraviolet lamp 1. At the same time, the ultraviolet radiation generates ozone in the oxygen-containing gas in gas conduit 3. Permeate chamber 5 is separated from gas conduit 3 such that no mixing of the liquid and gas occurs. The filtered and radiated liquid is removed from permeate chamber 5 through liquid removal line 11. The ozone-containing gas is removed from gas conduit 3 through gas removal line 10. The ozone-containing gas and filtered and radiated liquid are fed through gas removal line 10 and liquid removal line 11, respectively, to ozone injection system 12 in which the ozone-containing gas is thoroughly mixed with the filtered and sterilized liquid. The ozone eliminates any microorganisms remaining in the liquid. The ozone-containing liquid is then passed from the ozone injection system 12 to a dental instrument, through dental unit water line 13.

Ultraviolet lamp 1 may be any lamp that generates germicidal ultraviolet emission at a wavelength and energy level that will induce the formation of ozone in an oxygen-containing gas. The shorter the wavelength spectrum, the higher the amount of ultraviolet radiation generated. A 254 nm lamp has been shown to be capable of initiating photo-oxidation, however, at this wavelength, only nominal sterilization occurs. The 185 nm lamp energy levels are sufficient to produce free radicals in varying degrees of photochemical excitement, such as excited hydroxy radicals (●HO) and hyperoxy radicals (●HO$_2$). By incorporating the shorter 185 nm wavelength, a higher energy intensity dosage is maintained, thus rapidly oxidizing any organic molecules by breaking chemical bonds. The subsequent chemical reaction, inducing the free radical, often produces chain reactions. This energy, at proper dosage levels, oxidizes any organic matter to oxygen ($O_2$).

The generation of ozone by shortwave ultraviolet radiation take place in the spectral region of 120 nm to 242 nm, with a peak output at 150 nm to 160 nm. The 185 nm wavelength lamp produces approximately 0.5 grams per hour of ozone per 425 ma lamp, in dry air. In view of these dual considerations, ultraviolet lamp 1 should be one capable of producing radiation in a first wavelength range of about 200 nanometers to about 300 nanometers in order to effectively kill most microorganisms such as airborne and surface bacteria, viruses, yeasts and molds, and in a second wavelength range of about 120 nanometers to about 242 nanometers to induce the generation of a sufficient amount of ozone in the oxygen-containing gas. The ultraviolet lamp can be, for example, a low pressure mercury lamp. The oxygen-containing gas is preferably ambient air which comprises about 21%, by volume oxygen. Air flow through gas conduit 3 can be adjusted to optimize ozone production.

Ultraviolet lamp 1 is disposed within ultraviolet radiation permeable sleeve 2. The sleeve can be in the shape of a tube and formed of quartz glass. Alternatively, the sleeve may be formed from hard glass, soft glass, transparent or translucent ultraviolet resistant plastic (e.g., polytetrafluoroethylene, polyvinylfluoride or polycarbonate. Sleeve 2 is sealed to prevent liquid in permeate chamber 5 from mixing with the gas in gas conduit 3. Sleeve 2 may be sealed to end plate 11. End plate 11 can be sealed about either the inner wall, outer wall or both of sleeve 2. The sealing can be accomplished by any conventional sealing means such as (1) an elastomeric seal (e.g., at least one o-ring, a grommet, a gland, or a mechanical seal), (2) a packing such as gland packing or a mechanical seal, (3) compression fitting such as a Swagelock™ or similar fitting compression right is made of any suitable polymeric, elastomeric or metallic material, or (4) any type of non-toxic chemical adhesive, potting, hot melt or thermostatic material.

Filtration member 4 can be formed from at least one material selected from the group consisting of: activated carbon, activated carbon block, adsorption resins, ion exchange resins, zeolite, reduction catalysts, paper, polymers, clay, ceramics, metals, nylon, wood pulp, cellulose, cotton, fibers, and any other material capable of separating particulate, organics or inorganics from a feed stream. Filtration member 4 is preferably in the form of one of the following: string wound filter, fiber composite molded filter, pleated filter, hollow fiber membrane, spiral wound membrane, plate and frame membrane and any other conventional form desired by the user.

When filtration member 4 is used to remove organic materials, such as benzene, it is preferably formed of activated carbon or adsorption resin. To remove inorganic materials, such as heavy metals, or sulfites, filtration member 4 should be formed from ion exchange resin, zeolite or a reduction catalyst.

Air drying device 25 can be a desiccating compound, a molecular sieve, a heater, a membrane drying unit (water selective membrane) or other suitable drying means. Oxygen concentrating device 26 can comprise a swing adsorption unit or an oxygen selective membrane unit.

Figure 2:
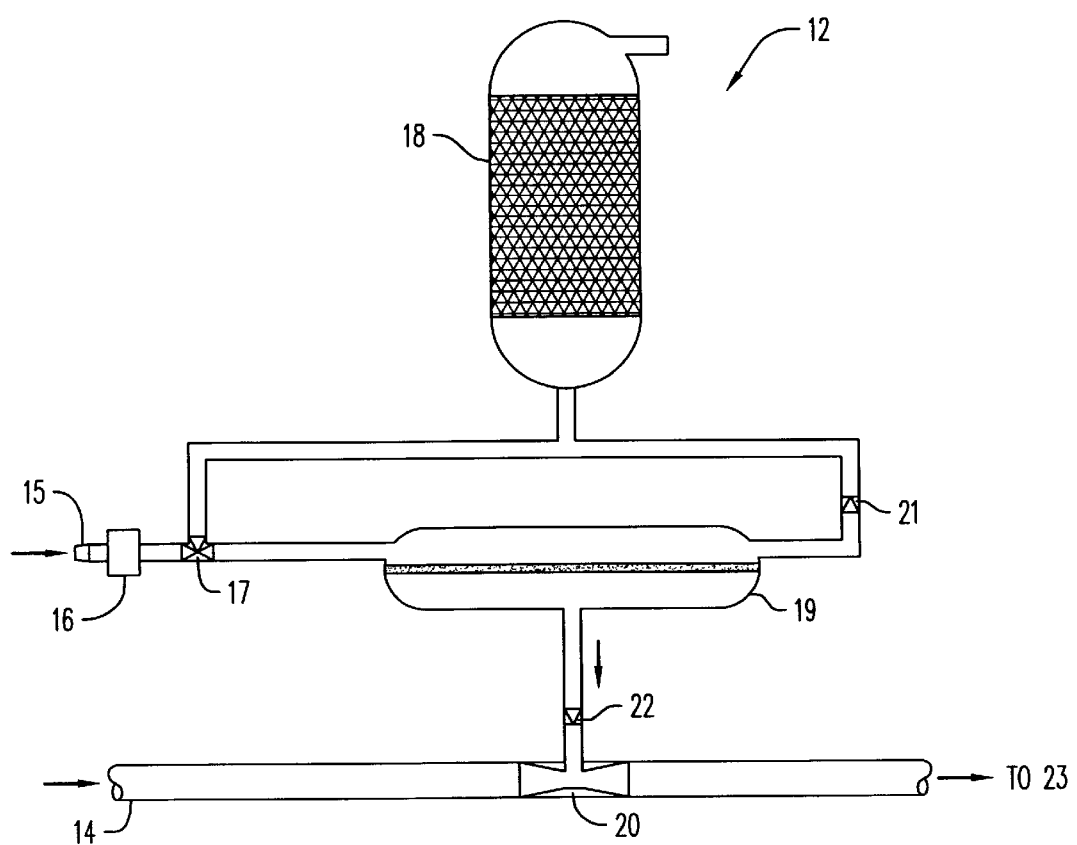
FIG. 2 is a diagram of an ozone injection system suitable for use as a component of the apparatus of the present invention.

Ozone-containing gas removed through gas removal line 10 and the filtered and radiated liquid removed through liquid removal line 11, are combined in ozone injection system 12. Ozone injection system 12 can best be understood with reference to FIG. 2, FIG. 3 or FIG. 4. FIG. 2 is a diagram of an ozone injection system suitable for use as a component of the apparatus of the present invention. In the ozone injection system of FIG. 2, the treated and filtered liquid is fed through liquid removal line 11 to liquid inlet 14, while the ozone-containing gas is fed from gas removal line 11 to gas inlet 15. Preferably, connection of gas removal line 11 to gas inlet 15 will be made through a coupling, such as Luer fitting 16 to facilitate quick installation and replacement.

The oxygen-containing gas passes through Luer fitting 16 to a three-way valve 17 connected between an ozone scrubber 18, which can be, for example, a carbon capsule, and a membrane contactor 19 such as a selective membrane contactor or a hydrophobic membrane contactor. Ozone has a water solubility 12 times higher than that of oxygen. The injection of the ozone-containing gas into the liquid via a selective membrane reduces the amount of non-active gas entering the liquid and results in a superior mixing of liquid and oxidant. The improved mixing of ozone in the liquid enables the ozone to contact all internal surfaces of the waterlines to provide for the efficient destruction of any biofilm constituents. Ozone is mixed with the filtered and radiated liquid via venturi tube 20. Check valves 21, 22 are used to prevent unwanted backflow within ozone injection system 12.

Figure 3:
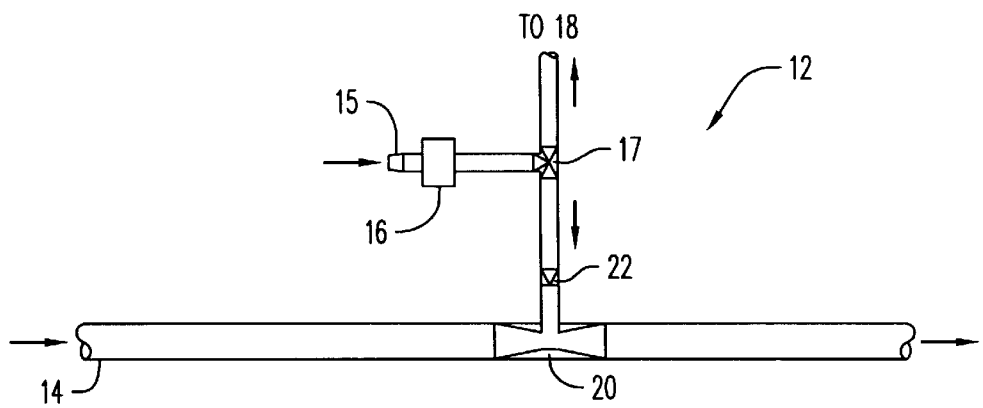
FIG. 3 is a diagram of an alternative ozone injection system suitable for use as a component of the apparatus of the present invention.
Figure 4:
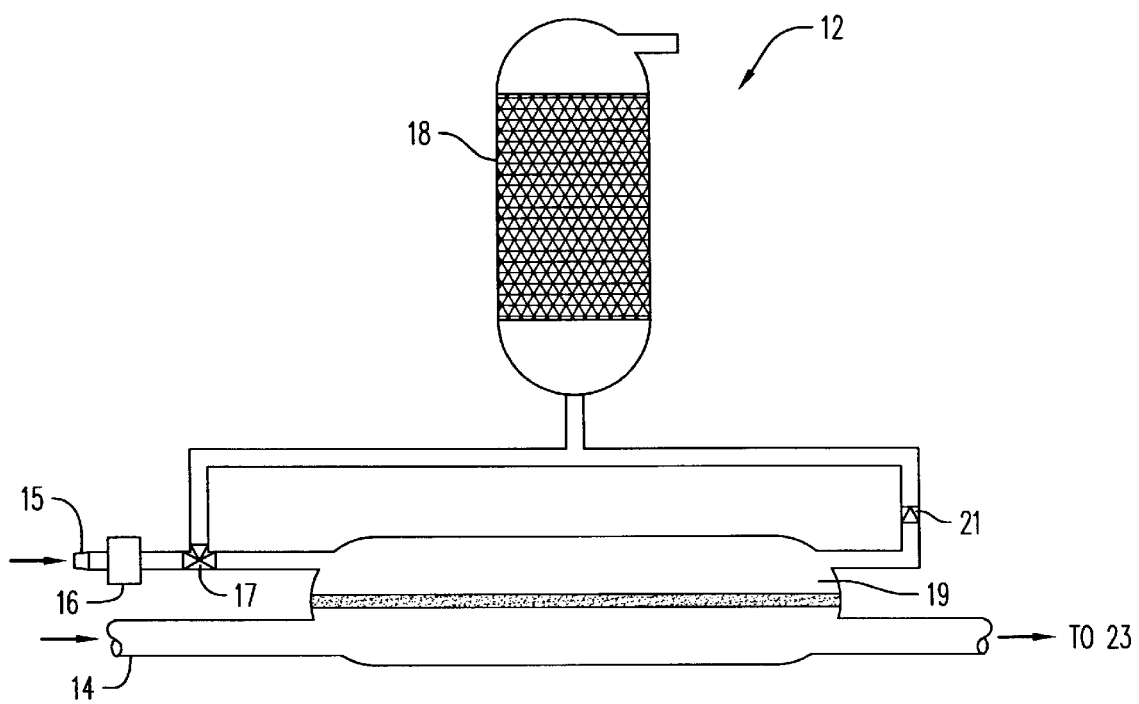
FIG. 4 is a diagram of a second alternative ozone injection system configuration.

Alternatively, as shown in FIG. 3, ozone injection system 12 can be provided without a membrane contactor, or, as shown in FIG. 4, membrane contactor 19 can be provided in direct contact with liquid removal line 11.

From ozone injection system 12, the ozone treated liquid is fed through dental unit water line 13 to a dental unit 23, such as a dental drill. Preferably, ozone injection occurs periodically, and simultaneous to the flushing of the dental unit water line 13 when the dental unit not used to avoid damage to dental materials and ionic interference with dental work, a problem associated with the continuous injection of chemical oxidants. This periodic injection of ozone can be actuated automatically or semi-automatically with the ability of a manual override.

While I have shown and described several embodiments in accordance with my invention, it is to clearly understood that the same are susceptible to numerous changes apparent to one skilled in the art. Therefore, I do not wish to be limited to the details shown and described but intend to show all changes and modifications which come within the scope of the appended claims.

What is claimed is:

1. An integrated filtration and sterilization apparatus comprising:

an ultraviolet lamp disposed within an ultraviolet radiation permeable sleeve such that a gas conduit is formed between an outer surface of said ultraviolet lamp and an inner surface of said sleeve;

a filtration member disposed about said sleeve such that a permeate chamber is formed between an outer surface of said sleeve and an inner surface of said filtration member;

a feed chamber disposed about an outer surface of said filtration member;

means for feeding a liquid to said feed chamber and removing liquid from said permeate chamber;

means for feeding an oxygen-containing gas to, and removing an ozone-containing gas from said gas conduit; and an ozone injection system for mixing liquid removed from said permeate chamber and ozone-containing gas from said gas conduit downstream from said permeate chamber, said ozone injection system comprising:
- at least one component selected from the group consisting of a selective membrane contactor and a hydrophobic membrane contactor; and
- means for periodically actuating an injection of ozone into a waterline downstream of said permeate chamber.

2. The apparatus of claim 1 wherein said ultraviolet lamp generates ultraviolet radiation in a first wavelength range of about 200 nanometers to about 300 nanometers, and a second wavelength range of about 120 nanometers to about 242 nanometers.

3. The apparatus of claim 2 wherein said second wavelength range is about 150 nanometers to about 160 nanometers.

4. The apparatus of claim 1, wherein said ultraviolet lamp is a low pressure mercury lamp.

5. The apparatus of claim 1 wherein said gas conduit is sealed from said permeate chamber such that liquid in said permeate chamber does not mix with gas in said gas conduit.

6. The apparatus of claim 5, wherein said gas conduit is formed as a tube.

7. The apparatus of claim 6, wherein said tube is formed of an ultraviolet radiation permeable material selected from the group consisting of quartz, hard glass, soft glass, and transparent or translucent ultraviolet resistant plastic.

8. The apparatus of claim 1, wherein said filtration member is formed from at least one material selected from the group consisting of activated carbon, activated carbon block, adsorption resins, ion exchange resins, zeolite, reduction catalysts, paper, polymers, clay, ceramics, metals, nylons, wood pulp, cellulose, cotton, and fibers.

9. The apparatus of claim 1, wherein said filtration member is in a form selected from the group consisting of string wound filter, fiber composite molded filter, pleated filter, hollow fiber membrane, spiral wound membrane, and plate and frame membrane.

10. The apparatus of claim 1 further comprising at least one component selected from the group consisting of a blower, a pump, an air drying device and an oxygen concentrating device.

11. A dental unit water supply system which comprises:
an integrated filtration and sterilization apparatus comprising:
- an ultraviolet lamp disposed within an ultraviolet radiation permeable sleeve such that a gas conduit is formed between an outer surface of said ultraviolet lamp and an inner surface of said sleeve;
- a filtration member disposed about said sleeve such that a permeate chamber is formed between an outer surface of said sleeve and an inner surface of said filtration member;
- a feed chamber disposed about an outer surface of said filtration member;
- means for feeding a liquid to said feed chamber and removing liquid from said permeate chamber;
- means for feeding an oxygen-containing gas to, and removing an ozone-containing gas from said gas conduit; and
- an ozone injection system for mixing liquid removed from said permeate chamber and ozone-containing gas from said gas conduit downstream from said permeate chamber, said ozone injection system comprising:
  - at least one component selected from the group consisting of a selective membrane contactor and a hydrophobic membrane contactor; and
  - means for periodically actuating an injection of ozone into a waterline downstream of said permeate chamber; and
means for supplying the mixed liquid to a dental unit.

12. The system of claim 11 wherein said ultraviolet lamp generates ultraviolet radiation in a first wavelength range of about 200 nanometers to about 300 nanometers, and a second wavelength range of about 120 nanometers to about 242 nanometers.

13. The system of claim 12 wherein said second wavelength range is about 150 nanometers to about 160 nanometers.

14. The system of claim 11, wherein said ultraviolet lamp is a low pressure mercury lamp.

15. The system of claim 11, wherein said ozone injection system comprises means to periodically inject ozone into a system line, simultaneous to the flushing of said line.

* * * * *